(12) United States Patent
Gledhill et al.

(10) Patent No.: US 9,383,304 B2
(45) Date of Patent: Jul. 5, 2016

(54) LABORATORY ASSESSMENT OF PDC CUTTER DESIGN UNDER MIXED-MODE CONDITIONS

(71) Applicant: Diamond Innovations, Inc., Worthington, OH (US)

(72) Inventors: Andrew Gledhill, Westerville, OH (US); Christopher Long, Westerville, OH (US); Joel Vaughn, Groveport, OH (US)

(73) Assignee: Diamond Innovations, Inc., Worthington, OH (US)

( * ) Notice: Subject to any disclaimer, the term of this patent is extended or adjusted under 35 U.S.C. 154(b) by 321 days.

(21) Appl. No.: 13/791,165

(22) Filed: Mar. 8, 2013

(65) Prior Publication Data

US 2014/0250973 A1 Sep. 11, 2014

(51) Int. Cl.
*G05B 19/4065* (2006.01)
*G01N 3/56* (2006.01)
*G01N 3/58* (2006.01)

(52) U.S. Cl.
CPC .......... *G01N 3/565* (2013.01); *G01N 3/58* (2013.01); *G05B 19/4065* (2013.01)

(58) Field of Classification Search
CPC ....... E21B 10/567; E21B 12/02; E21B 10/46; E21B 47/01; G05B 19/4065; G05B 2219/34455; G05B 2219/37434
See application file for complete search history.

(56) References Cited

U.S. PATENT DOCUMENTS

| | | | | |
|---|---|---|---|---|
| 4,642,618 A * | 2/1987 | Johnson et al. | | 340/683 |
| 5,135,061 A * | 8/1992 | Newton, Jr. | | 175/428 |
| 5,216,917 A * | 6/1993 | Detournay | | 73/152.59 |
| 5,460,233 A * | 10/1995 | Meany et al. | | 175/428 |
| 5,544,713 A * | 8/1996 | Dennis | | 175/434 |
| 5,864,058 A * | 1/1999 | Chen | | 73/152.47 |
| 8,216,677 B2 * | 7/2012 | Mukhopadhyay et al. | ... | 428/408 |
| 8,875,591 B1 * | 11/2014 | Rodriguez | | 73/866 |
| 2006/0236616 A1 * | 10/2006 | Wan | | 51/309 |
| 2008/0023231 A1 * | 1/2008 | Vail | | 175/434 |
| 2011/0031036 A1 * | 2/2011 | Patel | | 175/430 |

(Continued)

FOREIGN PATENT DOCUMENTS

| | | | |
|---|---|---|---|
| WO | 0037909 A1 † | 6/2000 | |
| WO | 2011075479 A1 | 6/2011 | |
| WO | 2011124960 A1 | 10/2011 | |
| WO | 2011124984 A2 | 10/2011 | |

OTHER PUBLICATIONS

Werschmoeller et al., "Measurement of tool internal temperatures in the tool—chip contact region by embedded micro thin film thermocouples", Journal of Manufacturing Processes, No. 13, Jul. 30, 2011.*
Robert Radke, "New High Strength and Faster Drilling TSP Diamond Cutters", TEchnology International, Inc., Jul. 2006.*
Guha et al., "Wireless acquisition of temperature data from embedded thin film sensors in cutting insert", Journal of Manufacturing Processes, No. 14, Jun. 9, 2012.*
Durrand et al., "Super-hard, Thick, Shaped PDC Cutters for Hard Rock Drilling Development and Test Results", Proceedings of the 35th Workshop on Geothermal Reservoir Engineering, Feb. 1-3, 2010.*

(Continued)

*Primary Examiner* — David A Rogers

(57) ABSTRACT

A system and a method of testing a superabrasive cutter are disclosed. The system of testing a superabrasive cutter may comprise a spinning wheel holding the superabrasive cutter; a rock feeding into a rotation of the superabrasive cutter on the spinning wheel; and a plurality of sensors operably attaching to the spinning wheel and the rock to detect properties of the superabrasive cutter. The method of testing a superabrasive cutter may comprise steps of attaching a superabrasive cutter to a spinning wheel; moving a rock into a rotation of the superabrasive cutter on the spinning wheel; and communicably coupling a first sensor to the superabrasive cutter.

19 Claims, 11 Drawing Sheets

(56) References Cited

U.S. PATENT DOCUMENTS

| | | | |
|---|---|---|---|
| 2011/0063122 A1* | 3/2011 | Matsubara et al. | 340/679 |
| 2011/0222980 A1* | 9/2011 | Kuo et al. | 409/80 |
| 2011/0239764 A1 | 10/2011 | Bellin | |
| 2011/0239767 A1 | 10/2011 | Bellin | |
| 2011/0246096 A1 | 10/2011 | Bellin | |
| 2012/0132471 A1* | 5/2012 | Zhang et al. | 175/338 |
| 2012/0325564 A1* | 12/2012 | Vaughn et al. | 175/428 |

OTHER PUBLICATIONS

Demeng Che, Peidong Han, Ping Guo and Kornel Ehmann, Issues in Polycrystalline Diamond Curtter-Rock Interaction From a Metal Machining Point of View—Part I: Temperature, Stresses and Forces, Journal of Manufacturing Science and Engineering, Dec. 2012, vol. 134 pp. 064001-1-064001-10.†

John T. Finger, David A Glowka, PDC Bit Research at Sandia National Laboratories, Sandia Report, Printed Jun. 1989.†

\* cited by examiner

† cited by third party

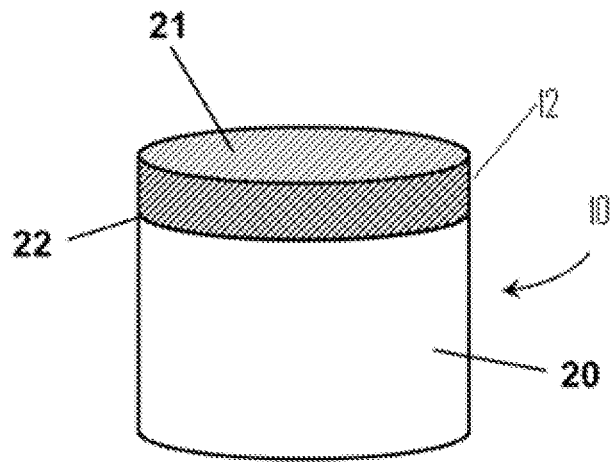
FIG. 1 – PRIOR ART
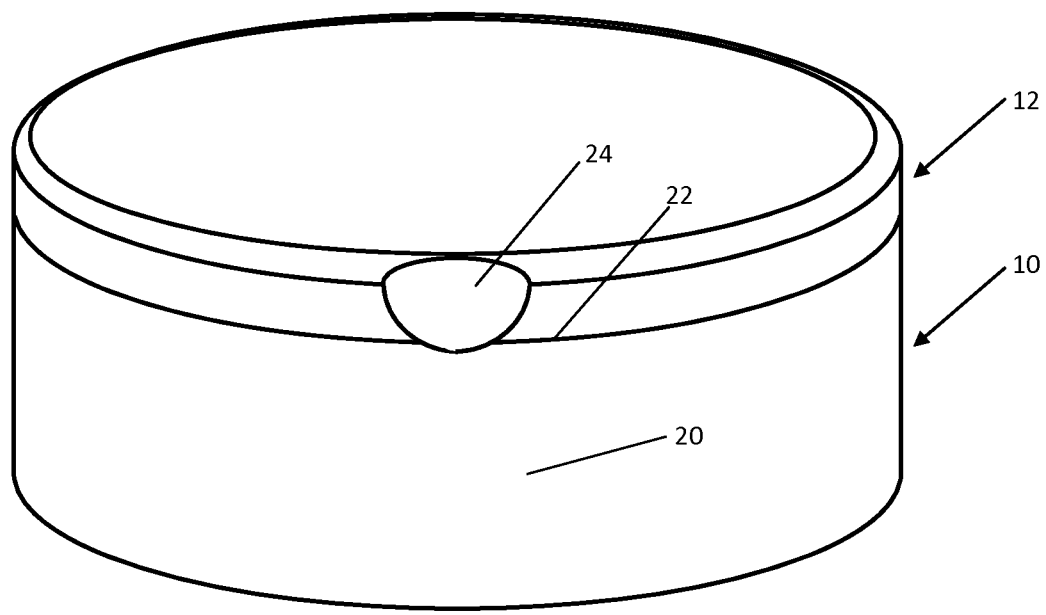
FIG. 2a – PRIOR ART

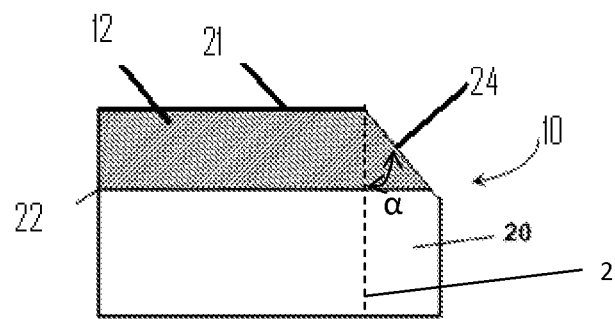
FIG. 2b – PRIOR ART
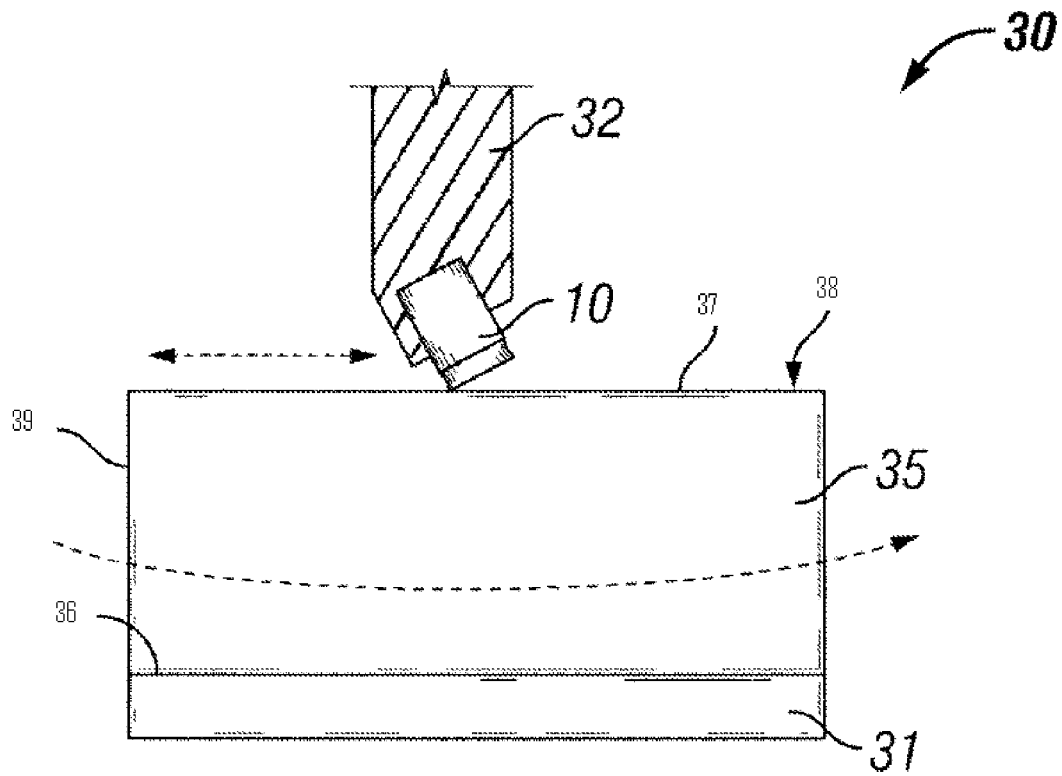
FIG. 3 – PRIOR ART

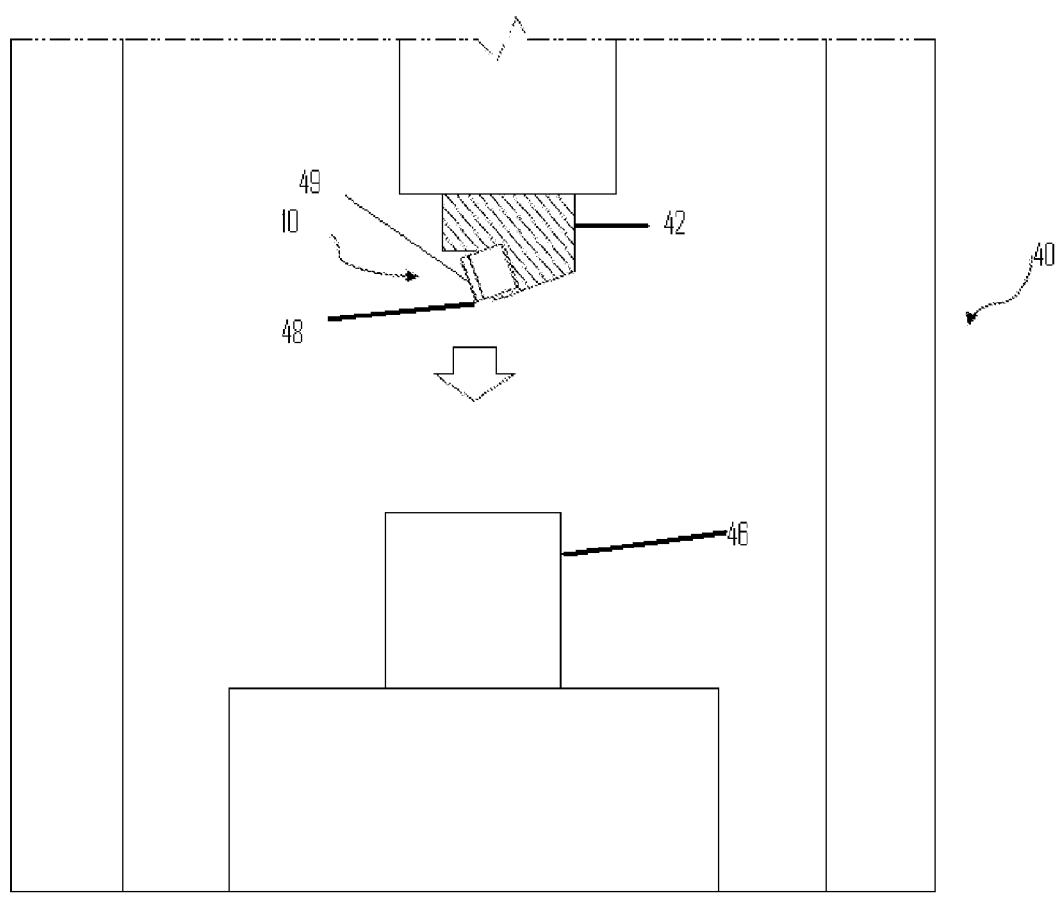
FIG. 4 – PRIOR ART

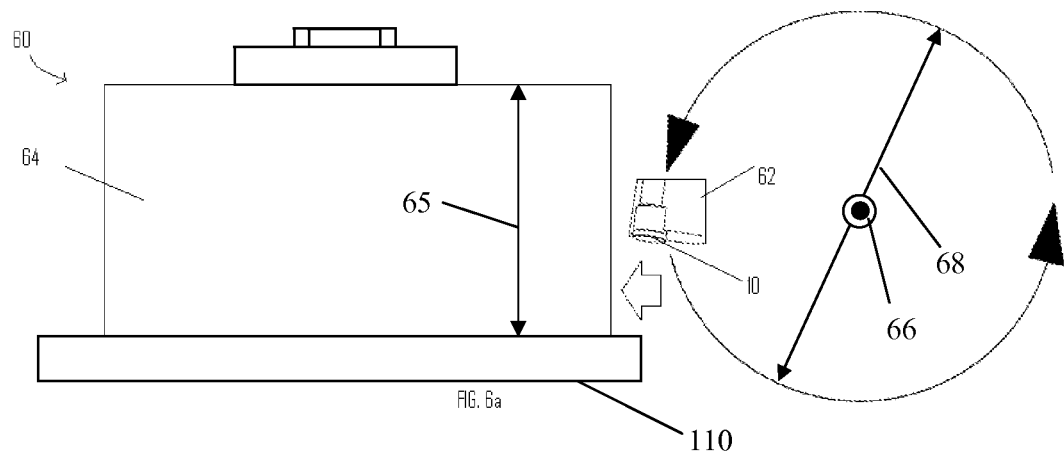
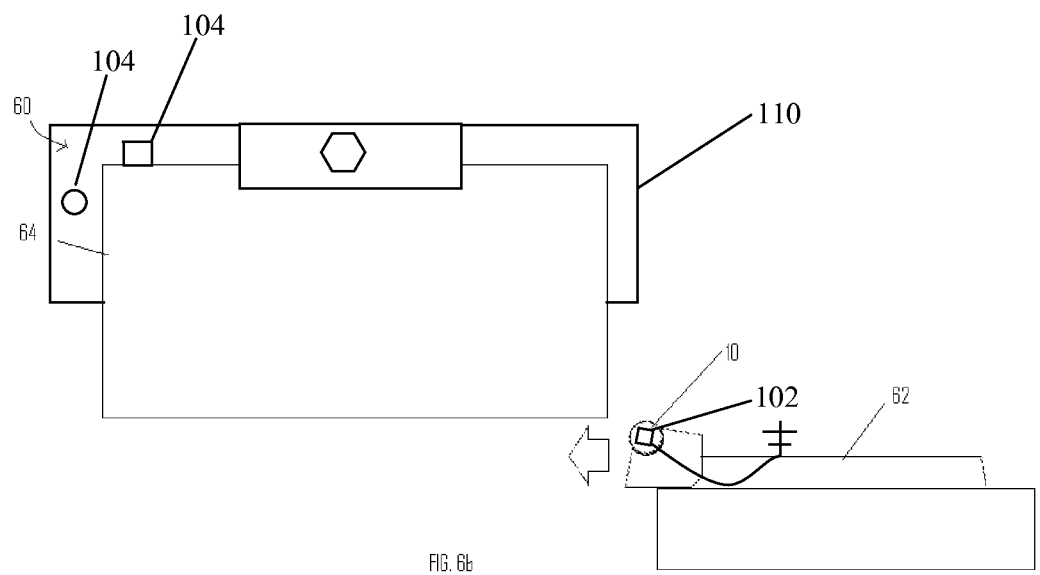

LABORATORY ASSESSMENT OF PDC CUTTER DESIGN UNDER MIXED-MODE CONDITIONS

TECHNICAL FIELD AND INDUSTRIAL APPLICABILITY

The present invention relates generally to a method and apparatus for testing superhard components; and more particularly, to a method and apparatus for testing the abrasive wear resistance and the impact resistance of superhard components.

Polycrystalline cubic boron nitride (PcBN), diamond and diamond composite materials are commonly used to provide a superhard cutting edge for cutting tools such as those used in metal machining, or rock drilling.

A "drop test" method by itself embodies drawbacks in that this method requires that many cutters be tested to achieve a valid statistical sampling that may compare the relative impact resistance of one cutter type to another cutter type. The test is inadequate in providing results that reflect the true impact resistance of the entire cutter as it would see impact loads in a downhole environment.

Therefore, it can be seen that there is a need for a superabrasive cutter and a method of testing the superabrasive cutter.

SUMMARY

In one embodiment, a system of testing a superabrasive cutter may comprise a spinning wheel holding the superabrasive cutter; a rock feeding into a rotation of the superabrasive cutter on the spinning wheel; and a plurality of sensors operably attaching to the spinning wheel and the rock to detect properties of the superabrasive cutter.

In another embodiment, a method may comprise steps of attaching a superabrasive cutter to a spinning wheel; moving a rock into a rotation of the superabrasive cutter on the spinning wheel; and communicably coupling a first sensor to the superabrasive cutter.

In yet another embodiment, a method of testing superabrasive material may comprise steps of rotating a superabrasive cutter with a spinning wheel, wherein the superabrasive cutter has a superabrasive volume and a metal carbide attached to the superabrasive volume; and moving a rock into the rotation of the superabrasive cutter until the superabrasive cutter wears to about at least 4 mm of the cemented tungsten carbide.

BRIEF DESCRIPTION OF THE DRAWINGS

The foregoing summary, as well as the following detailed description of the embodiments, will be better understood when read in conjunction with the appended drawings. It should be understood that the embodiments depicted are not limited to the precise arrangements and instrumentalities shown.

FIG. 1 is schematic perspective view of a common cylindrical shape PDC cutter blank produced in a HPHT process;

FIG. 2a is a schematic perspective view of a superabrasive cutter with a slope according to another exemplary embodiment;

FIG. 2b is a cross-sectional view of a superabrasive cutter according to an exemplary embodiment as shown in FIG. 2;

FIG. 3 is a schematic view of testing abrasive wear resistance of superabrasive cutter using a vertical turret lathe test;

FIG. 4 is a drop tower apparatus for testing impact resistance of superabrasive cutter;

FIG. 6a is a schematic top view of testing superabrasive cutter using an interrupted mill test illustrating moving direction of the superabrasive cutter;

FIG. 6b is a schematic top view of testing superabrasive cutter by using an interrupted mill test;

DETAILED DESCRIPTION

Figure 5:
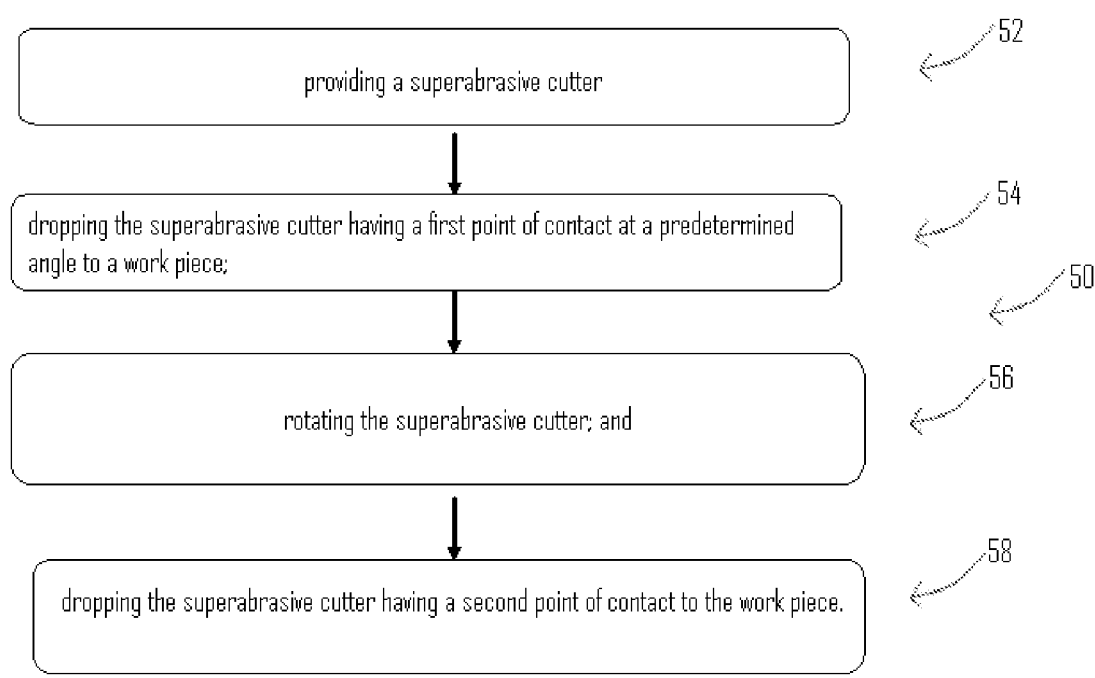
FIG. 5 is a flow chart illustrating a method of the drop test according to an exemplary embodiment.
Figure 7:
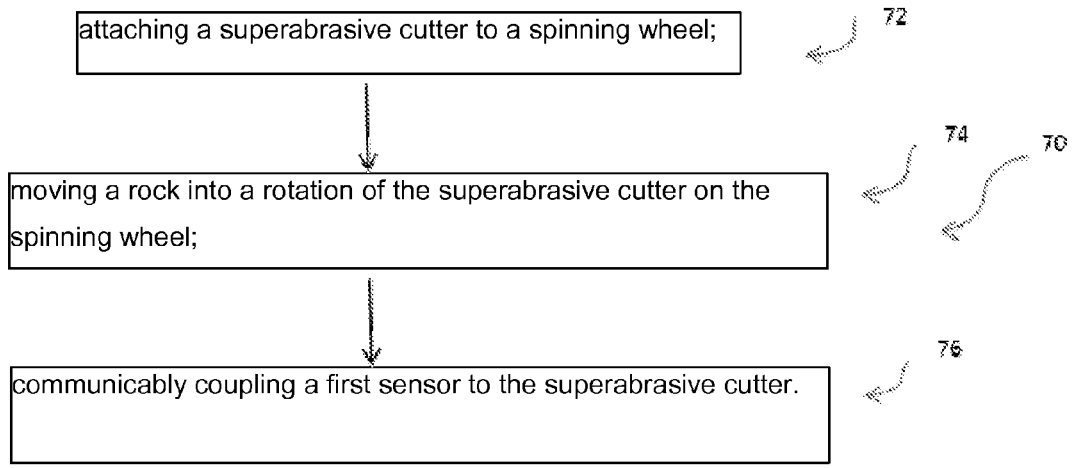
FIG. 7 is a flow chart illustrating a method of an interrupted mill test for a superabrasive cutter according to an exemplary embodiment.
Figure 8:
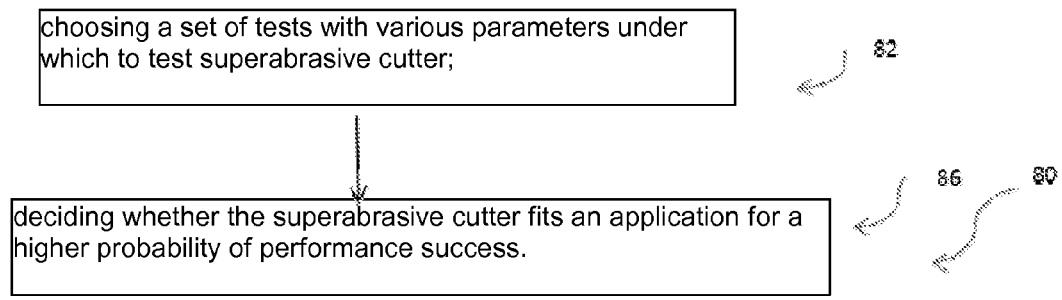
FIG. 8 is a flow chart illustrating a suite of test to choose from to test a superabrasive cutter according to an exemplary embodiment.

Before the present methods, systems and materials are described, it is to be understood that this disclosure is not limited to the particular methodologies, systems and materials described, as these may vary. It is also to be understood that the terminology used in the description is for the purpose of describing the particular versions or embodiments only, and is not intended to limit the scope. For example, as used herein, the singular forms "a," "an," and "the" include plural references unless the context clearly dictates otherwise. In addition, the word "comprising" as used herein is intended to mean "including but not limited to." Unless defined otherwise, all technical and scientific terms used herein have the same meanings as commonly understood by one of ordinary skill in the art.

Unless otherwise indicated, all numbers expressing quantities of ingredients, properties such as size, weight, reaction conditions and so forth used in the specification and claims are to the understood as being modified in all instances by the term "about". Accordingly, unless indicated to the contrary, the numerical parameters set forth in the following specification and attached claims are approximations that may vary depending upon the desired properties sought to be obtained by the invention. At the very least, and not as an attempt to limit the application of the doctrine of equivalents to the scope of the claims, each numerical parameter should at least be construed in light of the number of reported significant digits and by applying ordinary rounding techniques.

As used herein, the term "about" means plus or minus 10% of the numerical value of the number with which it is being used. Therefore, about 50 means in the range of 45-55.

As used herein, the term "superabrasive particles" may refer to ultra-hard particles or superabrasive particles having a Knoop hardness of 5000 KHN or greater. The superabrasive particles may include diamond, and cubic boron nitride, for example.

Polycrystalline diamond composite (or "PDC", as used hereafter) may represent a volume of crystalline diamond grains with embedded foreign material filling the inter-grain space. In one particular case, composite comprises crystalline diamond grains, bonded to each other by strong diamond-to-diamond bonds and forming a rigid polycrystalline diamond body, and the inter-grain regions, disposed between the bonded grains and filled with a catalyst material (e.g. cobalt or its alloys), which was used to promote diamond bonding during fabrication. Suitable metal solvent catalysts may include the metal in Group VIII of the Periodic table. PDC cutting element (or "PDC cutter", as is used thereafter) comprises an above mentioned polycrystalline diamond body attached to a suitable support substrate, e.g. cemented cobalt tungsten carbide (WC—Co), by virtue of the presence of cobalt metal. In another particular case, polycrystalline diamond composite comprises a plurality of crystalline diamond grains, which are not bonded to each other, but instead are bound together by foreign bonding materials such as borides, nitrides, carbides, e.g. SiC.

Polycrystalline diamond composites and PDC cutters may be fabricated in different ways and the following examples do not limit a variety of different types of diamond composites and PDC cutters which may be coated according to the exemplary embodiment. In one example, PDC cutters are formed by placing a mixture of diamond polycrystalline powder with a suitable solvent catalyst material (e.g. cobalt) on the top of WC—Co substrate, which assembly is subjected to processing conditions of extremely high pressure and high temperature (HPHT), where the solvent catalyst promotes desired inter-crystalline diamond-to-diamond bonding and, also, provides a binding between polycrystalline diamond body and substrate support. In another example, PDC cutter is formed by placing diamond powder without a catalyst material on the top of substrate containing a catalyst material (e.g. WC—Co substrate). In this example, necessary cobalt catalyst material is supplied from the substrate and melted cobalt is swept through the diamond powder during the HPHT process. In still another example, a hard polycrystalline diamond composite is fabricated by forming a mixture of diamond powder with silicon powder and mixture is subjected to HPHT process, thus forming a dense polycrystalline cutter where diamond particles are bound together by newly formed SiC material.

Abrasion resistance of polycrystalline diamond composites and PDC cutters may be determined mainly by the strength of bonding between diamond particles (e.g. cobalt catalyst), or, in the case when diamond-to-diamond bonding is absent, by foreign material working as a binder (e.g. SiC binder), or in still another case, by both diamond-to-diamond bonding and foreign binder.

The presence of some catalysts inside the polycrystalline diamond body of PDC cutter promotes the degradation of the cutting edge of the cutter during the cutting process, especially if the edge temperature reaches a high enough critical value. Probably, the cobalt driven degradation may be caused by the large difference in thermal expansion between diamond and catalyst (e.g. cobalt metal), and also by catalytic effect of cobalt on diamond graphitization. Removal of catalyst from the polycrystalline diamond body of PDC cutter, for example by chemical etching in acids, leaves an interconnected network of pores and a residual catalyst (up to 10 vol %) trapped inside the polycrystalline diamond body. It has been demonstrated that a chemically etched polycrystalline diamond cutter by removal of a substantial amount of cobalt from the PDC cutter significantly improves its abrasion resistance. Also it follows that a thicker cobalt depleted layer near the cutting edge provides better abrasion resistance of the PDC cutter than a thinner cobalt depleted layer.

Exemplary embodiments disclose a combination of laboratory testing methods including usage of a vertical turret lathe (VTL) operated under different conditions determined to expose a specific PDC cutter design to the following failure modes, edge wear, chipping, spalling, such as horizontal spalling, fracture, thermal, thermo-mechanical, fatigue, for example. In addition, the exemplary embodiments may use an impacting device to apply to cutters prepared in specific ways and use a mill device to apply to cutters prepared in specific ways. The test parameters and cutter configurations may be chosen to interrogate the cutter strengths and weaknesses regarding the failure modes likely encountered in subterranean drilling. The combination of test modes may provide the ability to tailor cutter design to drilling applications for a high probability of performance success.

Exemplary embodiments assess a combination of mixed-mode failures more likely to occur in the application. For example, a challenge to the cutter may be a combination of wear, chipping, fracture, thermal, spalling, and fatigue. A simple wear test and drop test may not assess the mixture of failure modes the cutter actually experiences. Nor does it adequately distinguish cutter designs which are likely to affect one combination of a failure mode vs. another failure mode. For example, if an application is known to cause primarily thermal-type failure in the cutters, but still requires significant abrasion resistance, but only modest fracture resistance, the exemplary embodiments permit assessing cutter designs which have a combination of simultaneous properties. Exemplary embodiments may provide a considerable advantage for designing and developing cutters which are more likely to perform better in a variety of drilling applications.

As shown in FIG. 1, a superabrasive cutter 10 which is insertable within a downhole tool (not shown) in according to an exemplary embodiment. One example of the superabrasive cutter 10 may include a superabrasive volume 12 having a top surface 21 and superabrasive particles. The superabrasive cutter 10 may include a substrate, such as a metal carbide 20, attached to the superabrasive volume 12 via an interface 22 between the superabrasive volume 12 and the metal carbide 20. The metal carbide 20 may be generally made from cemented cobalt tungsten carbide, or tungsten carbide, while the superabrasive volume 12 may be formed using a polycrystalline ultra-hard material layer, such as polycrystalline diamond ("POD"), polycrystalline cubic boron nitride ("PCBN"), or tungsten carbide mixed with diamond crystals (impregnated segments). The superabrasive particles may be selected from a group of cubic boron nitride, diamond, and diamond composite materials.

The superabrasive cutter 10 may be fabricated according to processes and materials known to persons having ordinary skill in the art. The cutting element 10 is referred to as a polycrystalline diamond compact ("PDC") cutter when polycrystalline diamond is used to form the polycrystalline volume 12. PDC cutters are known for their toughness and durability, which allow them to be an effective cutting insert in demanding applications. Although one type of superabrasive cutter 10 has been described, other types of superabrasive cutter 10 can be utilized. For example, in some embodiment, superabrasive cutter 10 may have a chamfer (not shown) around an outer peripheral of the top surface 21. The chamfer may have a vertical height of 0.5 mm and an angle of 45° degrees which may provide a particularly strong and fracture resistant tool component.

In some embodiment, as shown in FIG. 2a, the superabrasive cutter 10 may be a preform superabrasive cutter. The preform superabrasive cutter may further include a slope 24 situated from the top surface 21 of the superabrasive volume 12 toward the metal carbide 20. The preform superabrasive cutter may further include a chamfer having a vertical height of 0.5 mm and an angle of 45° degrees, for example. In some embodiment, the slope 24 may end in the superabrasive volume close to the interface 22. In another embodiment, the slope 24 may cross the interface 22 and end in the metal carbide 20.

As shown in FIG. 2b, the slope 24 may be flat and may be at an angle α degrees relative to a longitudinal axis 26. The angle α may be 5 to 18 degrees, for example, relative to a longitudinal axis 26 of the preform superabrasive cutter. In one exemplary embodiment, the angle may be 15 degrees relative to a longitudinal axis of the longitudinal axis 26. A vertical height of the slope 24 may be from 0.5 mm to 4 mm, for example.

Superabrasive cutter 10 may be tested for abrasive wear resistance through the use of testing methods, such as a vertical turret lathe (VTL), a drop test, and an interrupted mill test.

FIG. 3 shows a vertical turret lathe 30 for testing abrasive wear resistance of a superabrasive cutter 10 using a vertical turret lathe ("VTL") test. Although one exemplary apparatus configuration for the VTL 30 is provided, other apparatus configurations may be used without departing from the scope and spirit of the exemplary embodiment. The vertical turret lathe 30 may include a rotating table 31 and a tool holder 32 positioned above the rotating table 31. A granite work piece 35 has a first end 36, a second end 37, and a sidewall 39 extending from the first end 36 to the second end 37. According to the VTL test, second end 37 is an exposed surface 38 which makes contact with a superabrasive cutter's superabrasive volume 12 during the test. The granite workpiece 35 is typically about thirty inches to about sixty inches in diameter, but can be smaller or larger depending upon the testing requirements.

The first end 36 may be mounted on the lower rotating table 31 of the VTL 30, thereby having the exposed surface 38 face the tool holder 32. The PDC cutter 10 is mounted in the tool holder 32 above the granite workpiece's exposed surface 38 and makes contact with the exposed surface 38. The granite work piece 35 is rotated via the rotating table 31 as the tool holder 32 cycles the PDC cutter 10 from the edge of the granite work piece's exposed surface 38 to its center. The tool holder 32 has a predetermined downward feed rate. The cutter, with a rake angle −10 degrees, for example, is run across the rotating workpiece with a depth of cut of 0.010" at a speed of 300 surface feet per minute (sfpm), for example. The size of the wear land on the superabrasive cutter may be calculated after each pass of the workpiece. The volume of material removed from the workpiece is calculated.

In addition to testing for abrasive wear resistance, the superabrasive cutter 10 may also be tested for resistance to impact loading. FIG. 4 shows a drop tower apparatus 40 for testing impact resistance of superabrasive cutter 10 using a "drop test" method. The drop test method emulates the type of loading that may be encountered when the superabrasive cutter 10 transitions from one subterranean formation to another or experiences lateral and axial vibrations.

Referring to FIG. 4, the drop tower apparatus 40 includes a superabrasive cutter 10, such as a PDC cutter or preform superabrasive cutter, a target fixture or work piece 46, a holder 42 for the superabrasive cutter 10. The holder 42 may be fabricated from steel and may be positioned above the work piece 46. The work piece 46 may be made of materials, such as cemented tungsten carbide, steel, or superhard materials, such as polycrystalline diamond table.

The superabrasive cutter 10 used may have a sharp edge, or a regular chamfer, or may have a slope as shown in FIGS. 2a and 2b. The superabrasive cutter 10 may be dropped down on the work piece 46 at a first point of contact of the superabrasive cutter 10. The test may also be referred to as a "side impact" test because the work piece 46 impacts an exposed edge of the diamond table or at the contact face between the diamond table and a metal carbide substrate. The "drop test" is very sensitive to the edge geometry of the diamond table. If the diamond table is slightly chamfered, the test results may be altered considerably. The total energy, expressed in Joules, expended to make the initial fracture in the diamond table is recorded. For more highly impact resistant superabrasive cutter 10, the superabrasive cutter 10 may be dropped according to a preset plan from increasing heights to impart greater energy on the work piece 46.

As shown in FIG. 5, a method 50 of testing a superabrasive cutter 10 by using a drop test may comprise steps of: providing a superabrasive cutter in a step 52; dropping the superabrasive cutter having a first point of contact 48 at a predetermined angle to a work piece in a step 54; rotating the superabrasive cutter in a step 56; and dropping the superabrasive cutter having a second point of contact 49 to the work piece in a step 58. The method of 50 may further include a step of continuing dropping the superabrasive cutter 10 until the superabrasive cutter 10 chips; a step of adjusting a height of the superabrasive cutter until the superabrasive cutter chips.

The superabrasive cutter 10 may have a diamond volume and metal carbide attached to the diamond volume. The diamond volume may contain the first point of contact 48 and the second point of contact 49 to the work piece 46. In one exemplary embodiment, the first point of contact and the second point of contact may be slopes, as shown in FIG. 2.

In another exemplary embodiment, a method of testing superabrasive material by the drop test may comprise steps of holding a superabrasive cutter at a predetermined height; and dropping the superabrasive cutter at various points of contact at a predetermined angle to a work piece until the superabrasive cutter chips; adjusting the predetermined height of the superabrasive cutter before dropping the superabrasive cutter. The various points of contact, such as slopes, may include a first point of contact and a second point of contact. The second point of contact is at a predetermined distance to the first point of contact such that impact from the first point of contact to the work piece does not affect the second point of contact. In one exemplary embodiment, the superabrasive cutter 10 may have four points of contact, for example.

As shown in FIGS. 6a and 6b of interrupted mill test, a system 60 of testing a superabrasive cutter 10 may comprise a spinning wheel 62 holding the superabrasive cutter, a rock 64 feeding into a rotation of the superabrasive cutter 10 on the spinning wheel 62, a plurality of sensors, such as a temperature sensor 102 and a vibration sensor 104, operably attaching to the spinning wheel 62 and the rock 64, respectively, to detect properties of the superabrasive cutter 10. As is depicted in FIG. 6a, the spinning wheel includes an axis of rotation 66 about which the superabrasive cutter 10 is rotated and a diameter of cutter rotation 68 through which the superabrasive cutter 10 is rotated. The diameter of cutter rotation 68 may be greater than a height 65 of the rock 64. In this interrupted mill test, the superabrasive cutter 10 may have a superabrasive volume, such as diamond table, which has a chamfer 0.012". During the test, the superabrasive cutter may be mounted in a steel holder. The temperature sensor 102 is a thermocouple clamped to the face of the cutter. The temperature sensor may be attached to a wireless transmitter, which sends a signal to a receiver, which is connected to a data collection computer. The vibration sensor 104 may be attached to a table 110, which holds the rock 64. Alternatively, the vibration sensor 104 may be attached to the back of the rock 64 that is the side opposite of the milling.

A method 70 of testing a superabrasive cutter by the interrupted mill test may comprise steps of attaching a superabrasive cutter 10 to a spinning wheel in a step 72; moving a rock into a rotation of the superabrasive cutter 10 on the spinning wheel in a step 74; and communicably coupling a first sensor, such as a temperature sensor; to the superabrasive cutter 10 in a step 76; communicably coupling a second sensor, such as a vibration sensor to the rock.

The method 70 may further include the superabrasive cutter plunging into the rock and removing an arc of material from the rock; and continuing machining the rock by the superabrasive cutter until the cutter wears to a half way of the tungsten carbide, such as at least 4 mm of the tungsten carbide, for example.

In another exemplary embodiment, a method of testing a superabrasive cutter may comprise steps of rotating a superabrasive cutter with a spinning wheel, wherein the superabrasive cutter has a superabrasive volume and a metal carbide attached to the superabrasive volume; and moving a rock into the rotation of the superabrasive cutter until the superabrasive cutter wears to a half way of the tungsten carbide.

To assess the performance of the superabrasive cutter, the superabrasive cutter may be tested in a set of tests with various parameters. The method 80 of testing of the superabrasive cutter may comprise steps of choosing a set of tests with various parameters under which to test superabrasive cutter in a step 82; and deciding whether the superabrasive cutter fits an application, such as a drilling application, for a high probability of performance success in a step 86. The set of tests may comprise at least one of vertical turret lathe test, an interrupted mill test, and a drop test. The various parameters may include speed, depth of cut, cross feed, a tool holder for vertical turret lathe test and the interrupted mill test. The various parameters may further include a height of a holder for the superabrasive cutter, work piece wherein the work piece is a target of the superabrasive cutter for the drop test.

In another exemplary embodiment, a method of testing a superabrasive cutter may comprise steps of designing a set of tests with various parameters to test superabrasive cutter; and changing testing conditions of the superabrasive cutter with the various parameters to simulate an application. In yet another exemplary embodiment, a method of testing a superabrasive cutter may comprise steps of choosing a set of tests to test the superabrasive cutter depending on an application, such as a drilling application; and deciding which superabrasive cutter best fit for the application.

Example 1

Conventional Testing (as Known from Prior Art)

PDC cutters were produced by the methods described in the prior art, composed of a starting diamond powder with an average grain size of 12 microns in diameter, or with an average grain size of 24 microns in diameter and a metal carbide, such as tungsten carbide, attached to the polycrystalline diamond via an interface between the polycrystalline diamond and tungsten carbide. The cutter was ground and finished to 16 mm in diameter, and 13 mm in height. A 45 degree bevel was placed on the edge of the diamond, with a thickness of about 0.4 mm. Some cutters had the majority of catalyst metal removed from the working surface of the diamond.

Figure 9A:
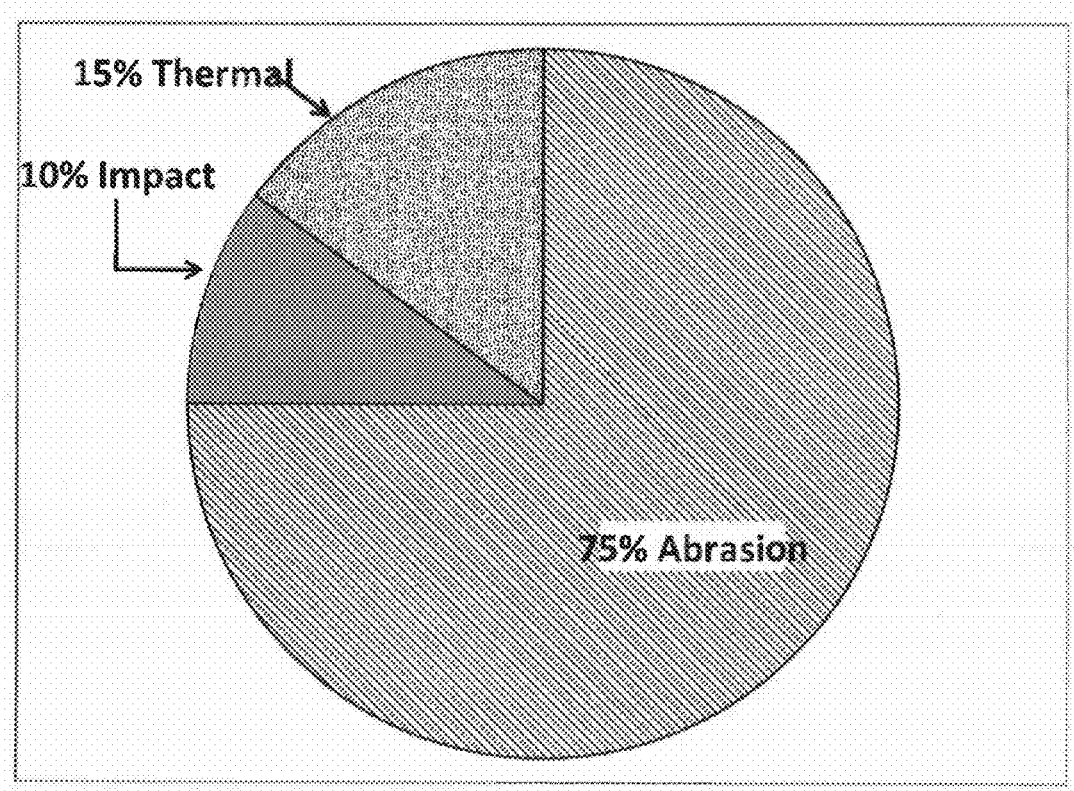
FIG. 9a is a pie chart illustrating a relationship among thermal mode, impact mode, and abrasion mode according to an exemplary embodiment.

The PDC cutter was tested on a vertical turret lathe (VTL) in the convention described in the prior art, referred to here as VTL-A as shown in FIG. 9a. The reference chart may have components of abrasion mode, thermal mode, and impact mode, for example. Specifically, the cutter was tested such that the depth of cut is between 0.010" and 0.030" in one example, between 0.015" and 0.017" in another example, under a continuous flood of cooling fluid. The table may be rotated at a variable speed such that the cutter machined a constant amount of linear feet per minute. The surface feet per minute were between 200 and 600 in one example, between 350 and 425 feet/minute in another example. The cutter was cross-fed into the rock at a constant rate between 0.100" and 0.200" per revolution of the table. The cutter was mounted into a fixture at an incline, with a rake angle between −5 and −20 degrees in one example, between −12 and −16 degrees in another example. The rock used in the test was a member of the granite family of rocks.

Testing of this nature involved several different damage mechanisms which contribute to the wear of cutters. The nature and chemical composition of the rock as well as the machine parameters contributed to the three major damage mechanisms: abrasive damage, thermal damage, and impact damage. In the VTL-A test as shown in FIG. 9a, the primary damage mode was abrasive wear, which was estimated to comprise 75% of the damage. Thermal damage contributed an estimated 15% of the damage, and impact damage made up the remaining estimated 10% of the failure modes.

The cutter machined rock for a specified number of passes across the rock before stopping. The cutter was removed from the VTL, imaged with an optical microscope, and the volume of material removed from the cutter was calculated from the image. The cutter was then remounted to the VTL, and additional passes machining rock were performed until the test reached a predetermined number of passes or the wear in the cutter extends through the entirety of the tungsten carbide. Additionally, the frequency of pictures allowed for detection of chips in the cutting edge of the PDC.

The volume of material removed as a function of rock removed was then compared to other cutters, and from this comparison, a determination was made as to the relative quality of the cutter.

Example 2

New Test Suite

A cutter was produced in the same fashion as example 1. This cutter was subjected to a suite of tests on the VTL to probe the strengths and weaknesses of that cutter in different failure modes. Specifically, the cutter may be tested in two or more VTL tests, aimed at determining how the cutter would perform under primarily abrasive loading, or under a high thermal load, or under high impact loading.

The cutter may undergo the VTL-A test described in Example 1 to determine the resistance to abrasive wear.

Figure 9B:
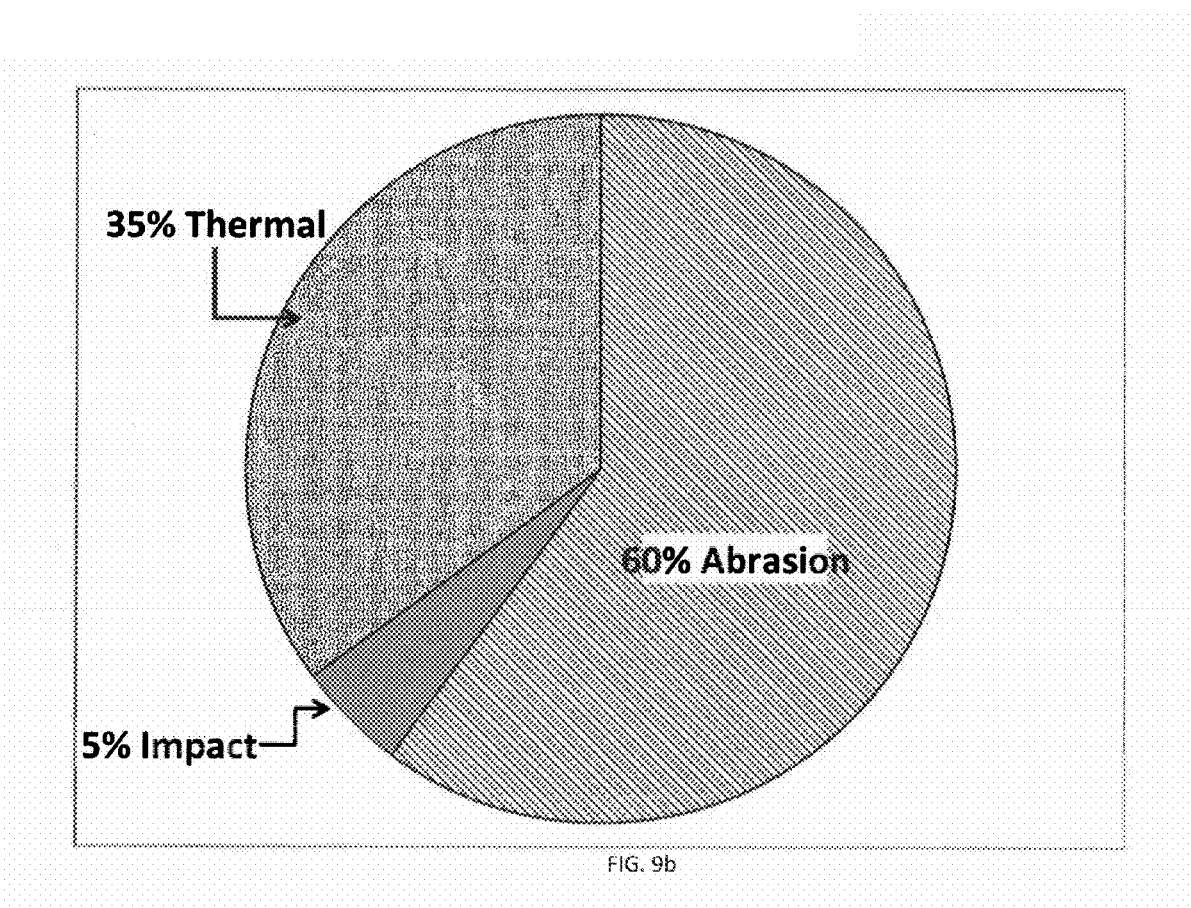
FIG. 9b is a pie chart illustrating a relationship among thermal mode, impact mode, and abrasion mode according to another exemplary embodiment.

Additionally, the cutter might undergo the VTL-B test as shown in FIG. 9b, which was designed to probe a cutter resistance to thermal damage. Specifically, the test involved mounting cutters on the VTL at a rake angle between −5 and −20 degrees in one exemplary embodiment, between −10 and −16 degrees in another exemplary embodiment, and machining granite at shallow depth of cut but at increased speeds under a flood of cooling water. The depth of cut was typically 0.005" to 0.020" in one example, between 0.008 and 0.011" in another example. The table rotated at a constant speed, between 20 and 80 RPM in one example, between 60 and 80 RPM in another example. The cross feed rate was held constant between 0.150" and 0.500" per revolution of the table in one example, between 0.250" and 0.400" in another example.

The constant table speed and increased cross feed rate resulted in a variable rate of surface feet of rock machined per minute throughout a pass across the rock, subjecting a cutter to a complex thermal cycle, which imparted a high thermal load on cutters at the beginning of each pass, and gradually decreased as the cutter moved towards the center of the table. The result was an estimated 35% contribution to the damage from thermal loading, 60% from abrasive damage, and 5% from impact damage.

The cutter machined rock for a specified number of passes across the rock before stopping. The cutter was removed from the VTL, imaged with an optical microscope, and the volume of material removed from the cutter was calculated from the image. The cutter was then remounted to the VTL, and additional passes machining rock were performed until the test reached a predetermined number of passes or the wear in the cutter extends through the entirety of the tungsten carbide. Additionally, the frequency of pictures allowed for detection of chips in the cutting edge of the PDC, which could show weakness in diamond sintering at elevated thermal loading.

Figure 9C:
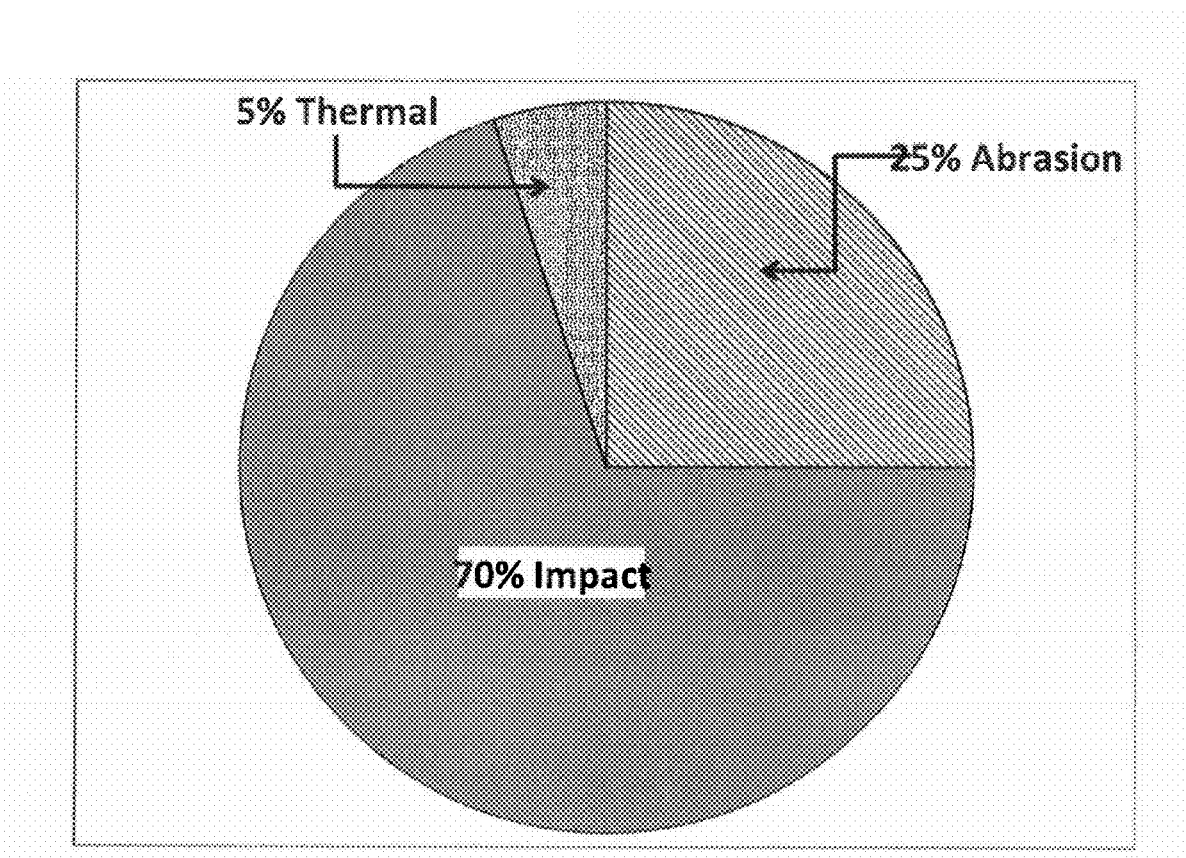
FIG. 9c is a pie chart illustrating a relationship among thermal mode, impact mode, and abrasion mode according to yet another exemplary embodiment.

Additionally, the cutter might undergo the VTL-C test as shown in FIG. 9c, which was designed to probe a cutter resistance to impact damage. Specifically, cutters were mounted onto a long sample mounting arm between 4" and 8" longer than conventional mounting, at a rake angle between −5 and −20 degrees in one example, between −7 and −15 degrees in another example. Cutters were used to machine a granite rock under a constant flood of cooling water. The long sample holder was designed such that the shaft could flex slightly during the machining of the rock, imparting additional vibration and ultimately impact damage upon the cutter. The depth of cut for this test was increased significantly to between 0.040" and 0.100" in one example, between 0.080" and 0.100" in another example. The table was controlled to provide a constant amount of linear feet of rock machined as the cutter works towards the center of the rock at a rate of 100 to 300 surface feet per minute in one example, between 100 and 200 surface feet per minute in another example. The cross feed was held constant at a speed between 0.100" and 0.300" per revolution of the table in one example, between 0.100" and 0.200" in another example per revolution of the table.

The increased depth of cut and decreased machining rate resulted in a low thermal load, and increased impact imparted on the cutter. An estimated 70% of the damage present was from impact damage. An estimated 25% of the damage was from abrasion, and only 5% of the observed damage was estimated to be from thermal damage.

In the VTL-C test as shown in FIG. 9c, cutters machined the rock for a single pass, then were removed, imaged with an optical microscope, and inspected for the presence of cracks or chips in the diamond. With the high impact loading imparted by the test parameters, the onset of cracking in the diamond table and number of passes before chipping or spalling events was recorded for each cutter. Cutters that ran a significantly high number of passes before a crack or chip forms were thereby deemed to be more impact resistant than cutters which fail earlier in the test.

When the prior art VTL-A test was performed, an assessment could be made as to the relative wear behavior between test cutters. However, when two or more of the tests, according to the present invention, had been completed on test cutters, a deeper, more useful understanding of the cutters' strengths and weaknesses had been gained. With this expanded knowledge, a cutter might be more successfully targeted towards drilling applications where it was expected to perform well. For example, the cutter made with 12 micron diameter starting diamond might show excellent abrasion resistance, but poor impact resistance. The cutter made with 24 micron diameter diamond might show significantly better impact resistance, but at the expense of some abrasion resistance. With this information, the finer grain cutter could be targeted to applications where drilling requires high abrasion resistance, but has little impact component to the drilling. The coarser diamond cutter could be targeted to applications where drilling requires a high level of impact resistance and the abrasion resistance required is lower.

In another example, according to the present invention, a cutter made with 12 micron diameter starting diamond under particular synthesis conditions may show superior resistance to thermal failure compared to a cutter made with the same 12 micron diameter starting diamond but made under different synthesis conditions. Using the knowledge gained according to the present invention the cutter with the superior thermal resistance to failure would be targeted to applications where cutters experience a high level of temperature failure, such as in certain abrasive sandstones.

Example 3

Test Suite with Modified Measurement

A cutter was produced in the same fashion as example 1. This cutter was subjected to a suite of tests on the VTL according to the present invention to probe the strengths and weaknesses of that cutter in different failure modes. Specifically, the cutter might be tested in two or more VTL tests, aimed at determining how the cutter may perform under primarily abrasive loading, or under a high thermal load, or under high impact loading. A load cell to measure the normal and tangential forces is added to the sample mount in all of the VTL test runs, and data is collected for each test performed.

This test data gave valuable information about how efficiently a cutter is failing rock, thus can be used as a proxy for drilling efficiency when cutters are used to drill well holes for oil and gas extraction.

Interrupted Mill Examples

Example 1

Conventional Interrupted Mill Test

PDC cutters were produced by the methods described in the prior art, composed of a starting diamond powder with an average grain size of 12 microns in diameter, or with an average grain size of 24 microns in diameter. The cutter was ground and finished to 16 mm in diameter, and 13 mm in height. A 45 degree bevel was placed on the edge of the diamond, with a thickness of 0.4 mm. Some cutters had the majority of catalyst metal removed from the working surface of the diamond.

Cutters were subjected to an interrupted mill test, described in the prior art. Cutters were attached to a rapidly spinning wheel, rotating at between 300 and 600 rotations per minute in one example, between 500 and 600 rotations per minute in another example. The diameter of the cutter rotation was approximately 10", and was used to machine an 8" tall block of granite, 16" in length. The depth of cut was set between 0.050" and 0.200" and the granite was fed into the rotation at a rate between 1" per minute and 10" per minute. No coolant was used for the duration of the test. The test ended when the wear on the cutter extended through the diamond table and into the tungsten carbide, at which time the cutter rapidly heated and the cutting action was substantially reduced, resulting in vibration in the rock.

Figure 9D:
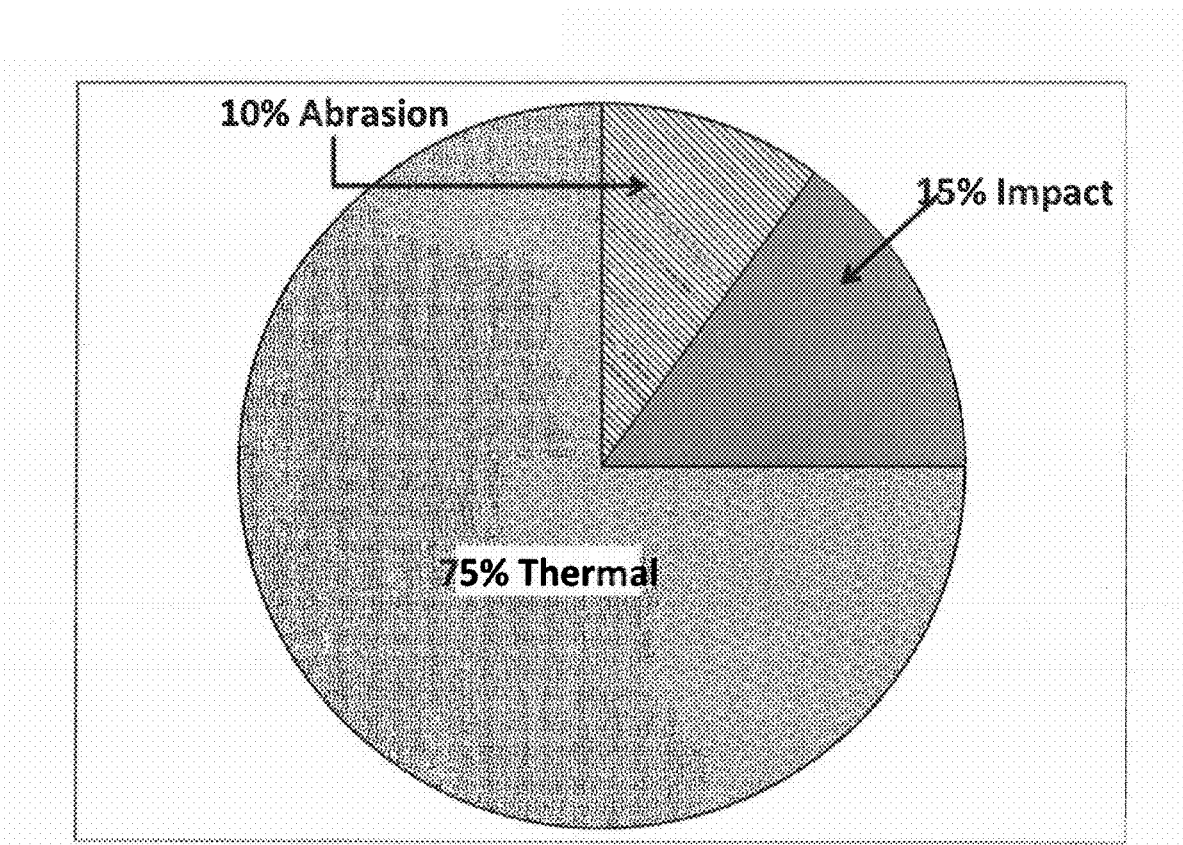
FIG. 9d is a pie chart illustrating a relationship among thermal mode, impact mode, and abrasion mode according to still another exemplary embodiment.

The geometry forced the cutter to repeatedly plunge into the rock, machined an arc of material, and then exit the rock. Running without coolant allows for extremely high levels of heat generated in the test. It was estimated that the thermal contribution to the failure of cutters in this test comprised 75% of the damage as shown in FIG. 9d. The impact of the cutter repeatedly plunging into the rock contributed an estimated 15% of the damage, and the abrasion of the granite block contributed an estimated 10% of the damage.

Cutters were scored based on the number of passes across the 16" block of rock before the cutter became inefficient at machining the rock, resulting in a high vibration of the mill. Cutters with high scores were deemed more thermally stable and thus targeted for applications where a high thermal load was expected.

According to the present invention, the VTL test suite in conjunction with the I-mill test provided a wide array of laboratory test conditions which measure the cutters' attributes. This expanded laboratory knowledge of cutter behavior provides a better means of targeting specific cutter designs to drilling applications where they are more likely to be successful.

Example 2

Interrupted Mill with Modified Data Collection

PDC cutters were produced as described in the previous example. To develop an understanding of the modes of cutter failure, the present invention described performing the interrupted milling test with the same test parameters as tabulated in Example 1 of Interrupted Mill Test, but with several key differences. Firstly, additional diagnostic tools had been employed to maximize both the quality and quantity of information collected during the test. Secondly, the criterion for stopping the test had been significantly altered.

Additional instrumentation was utilized to further the understanding of the damage mode observed in cutters. This was accomplished with the addition of an accelerometer to record vibration data at the back of the rock; that was the side of the rock opposite the milling. A thermocouple was clamped to the face of the cutter to record the thermal history of the cutter as the test progresses. The thermocouple was attached to a wireless transmitter, which sent the signal to a receiver which was connected to a data collection computer. Data was collected from each sensor at a rate between 100 and 5000 Hz in one exemplary embodiment, around 1000 Hz in another exemplary embodiment, and this data was then logged with a standard data recording software.

The present invention discloses an alternate ending to the test as well. In the prior art, testing was considered complete when the wear on the cutter extended through the diamond table and into the carbide. This extent of a wear scar decreased the cutting efficiency of the cutter, and resulted in increased vibration of the granite rock and mill. Cutters were then scored on the number of passes across the rock completed prior to this failure. With the addition of the vibration sensor, this level of vibration was easily detected, and cutters were allowed to wear until the wear scar extends through the thickness of the carbide substrate.

Figure 9E:
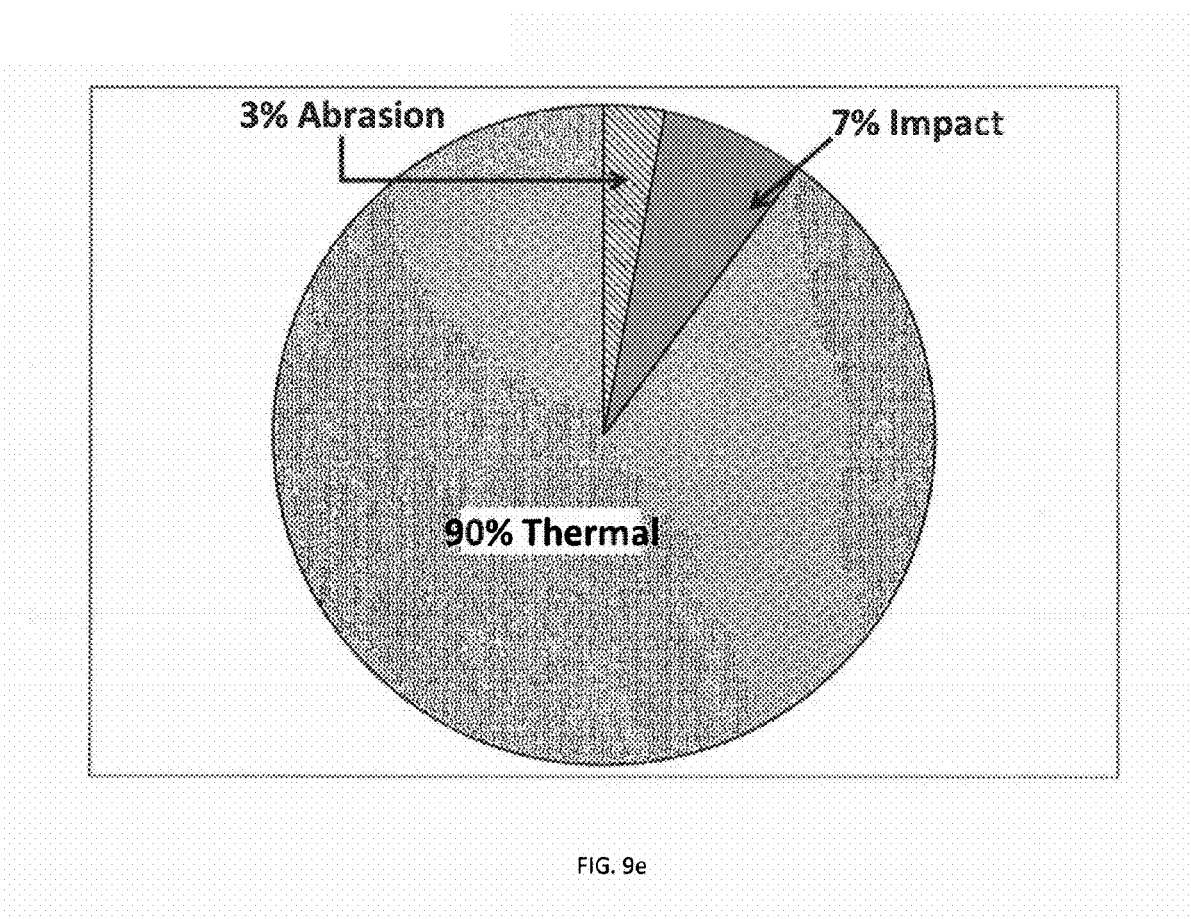
FIG. 9e is a pie chart illustrating a relationship among thermal mode, impact mode, and abrasion mode according to further another exemplary embodiment.

During this phase of the test, which progressed very quickly, the damage modes observed in the cutters drastically shifted. Namely, the amount of thermal degradation observed in the cutters was increased greatly; accounting for approximately 90% of the total damage, and the amount of impact and abrasive damage was decreased to approximately 7% and 3%, respectively, as shown in FIG. 9e.

The present invention taught that this increase in thermal damage allowed those skilled in the art to differentiate between cutters, and gave insight into how a cutter performed in highly thermal drilling applications. When this test was performed with other tests, such as conventional interrupted mill test or vertical turret lathe testing, one skilled in the art might assess the performance of a cutter with respect to the different observable damage modes, thereby allowing targeted application of a cutter to drilling locations where the cutter was well suited to maximize performance.

Impact Testing

Drop Testing

Example 1

Conventional Drop Test

To those skilled in the art, impact testing, or drop testing, was a known test which probes the strength of adhesion of a diamond table to the underlying carbide substrate. While the test serves as an excellent screening tool, and was often quantified as percentage of cutters which survive a given impact energy, it was not generally perceived to represent the observed damage from cutters used to drill holes for oil and gas production.

The conventional drop test, as described in the prior art, involved impacting a cutter, at an inclined angle, onto a work piece at a specified energy level. Typically, the inclination angle ranged from 5 to 20 degrees from the outer diameter of the cutter, and frequently the work piece was a hardened steel bar or plate. The cutter was impacted multiple times until delaminating fracture removed the bulk of the diamond table, or a maximum number of impacts was reached. Many multiples of each variety of cutter were required to complete a test set, as the fracture of ceramic materials typically occurred over a range of loads.

Typically, cutters were tested without a bevel or chamfer present on the surface of the diamond table. The use of a bevel significantly altered the energy required to break cutters, and as a result, the energy of impact required to fail a cutter was two to five times higher than a cutter without a bevel.

Example 2

Modified Drop Test

The present invention taught of a modified test, in which cutters were to be impact tested in the same configuration that they would be used in actual drilling applications. That was to say, the same dimensions, bevel size, and leach depth should be present on the test parts as the parts going into bits. The intention was to provide a quantifiable metric on the impact toughness of a cutter, which could be correlated into field performance.

Cutters were impacted at an inclination angle between 5 and 20 degrees from the outer diameter in one exemplary embodiment, around 15 degrees in another exemplary embodiment, onto a work piece which was substantially harder than the conventional tool steel. Typically, the work piece was chosen to be a tungsten carbide bar, cylinder, or plug. Alternatively, the work piece could be a sintered PDC compact. This harder work piece allowed for reasonable impact energies to be used with beveled cutters.

The testing procedure was substantially altered from the conventional testing. A single impact was made at a given energy, and if gross spallation or delamination was not observed, the cutter was rotated and dropped at a higher energy. This process was repeated until the energy of breakage was found. At energies below the breaking energy, cracking was clearly visible in the diamond table. Impacting again on the same region would extend these cracks and lead to a false failure reading. For this reason, the cutter might be rotated between impacts to allow for an uncracked region of the cutter to be probed. Typically, a maximum of four to five impacts might be performed on a cutter with 16 mm diameter to avoid the influence of previously cracked regions.

This test procedure was repeated across a statistically significant number of cutters, and the average failure load was reported. This failure load could then be compared to other cutters, resulting in a clear, quantified metric, which, when combined with other testing as described in the preceding examples, allowed the pairing of cutters to well suited drilling applications.

In addition to the failure load, the testing of the present invention allowed for the detection of the weakest area within a given cutter. For example, if the majority of cutters failed at the interface between diamond and the tungsten carbide support, this area could be deemed the weakest region, and effects to strengthen this weak link could be undertaken.

Example 3

Pre-Flat Drop Test

The present invention taught that impact damage might occur to a cutter at such a time as a significant wear scar had already developed on the cutter. An impact test had been developed to simulate such damage to cutters in a laboratory setting.

PDC cutters were produced by methods described in the prior art, and finished to the size, bevel and leach depth comparable to cutters used in down hole drilling applications. These cutters were then mounted in a fixture, and a diamond grinding wheel was used to produce one or more simulated wear scars on the cutter. The diamond grinding wheel could be run with coolant, to simulate a wear scar from an abrasive environment, or without coolant, which imparts significant heat into the cutter, simulating a high thermal-abrasive wear. The simulated wear scar could be ground at angles relevant to current bit designs, between 8 and 18 degrees. The size of the simulate scar could be adjusted in size to simulate small wear partially through the thickness of the diamond table, or large wear extending well into the carbide. Typically, the simulated wear scar was produced to extend just into the tungsten carbide support.

After the simulated wear scar was produced on the cutter as shown in FIGS. 2a and 2b, cutters were subjected to impact testing by the methods described in the prior two examples, with the simulated wear scar designated as the point of contact. The result was a test of the durability and toughness of the diamond leading edge, which could serve as a selection tool for placing the cutter into applications where the geology was ideal for a given cutter variety.

Example 4

Frontal Impact Test

In this embodiment, cutters with simulated wear flats as described in the preceding example, or cutters without simulated wear flats were impact tested, but at an angle 5 to 18 degrees from the top surface of the diamond table. Testing of this nature allowed for a different mode of failure to be observed in the cutters, allowing those skilled in the art to determine potential strengths and weaknesses in cutters, and provided guidance as to the placement of cutters into different drilling applications, especially when combined with other testing methodologies described in the preceding examples.

While reference has been made to specific embodiments, it is apparent that other embodiments and variations can be devised by others skilled in the art without departing from their spirit and scope. The appended claims are intended to be construed to include all such embodiments and equivalent variations.

The invention claimed is:

1. A system of testing a superabrasive cutter, comprising:
   a spinning wheel holding the superabrasive cutter, the spinning wheel comprising an axis of rotation about which the superabrasive cutter is rotated and a diameter of cutter rotation through which the superabrasive cutter is rotated;
   a rock having a surface that is positioned normal to the axis of rotation of the spinning wheel, wherein the rock is brought into contact with the superabrasive cutter and is fed in a direction normal to the axis of rotation of the spinning wheel, wherein the rock comprises a height evaluated in a plane of the diameter of cutter rotation, wherein the height of the rock is less than the diameter of cutter rotation; and
   a sensor operably coupled to the superabrasive cutter and a sensor operably coupled to the rock to detect a wear condition of the superabrasive cutter.

2. The system of claim 1, wherein the sensor operably coupled to the superabrasive cutter is a temperature sensor, the sensor operably coupled to the rock is a vibration sensor, and the wear condition of the superabrasive cutter corresponds to the temperature of the superabrasive cutter and a level of vibration of the rock for consistent cutting parameters.

3. The system of claim 2, further comprising a wireless transmitter connected to the temperature sensor.

4. The system of claim 2, wherein the vibration of the rock increases with increasing wear scar size.

5. The system of claim 2, wherein the temperature of the superabrasive cutter increase with increasing wear scar size.

6. The system of claim 1, wherein the superabrasive cutter has a superabrasive volume.

7. The system of claim 6, wherein the superabrasive volume has superabrasive particles.

8. The system of claim 6, wherein the superabrasive cutter has a metal carbide attached to the superabrasive volume via an interface between the superabrasive volume and the metal carbide.

9. The system of claim 8, wherein the metal carbide is cemented tungsten carbide.

10. A method of testing a superabrasive cutter, comprising:
    communicably coupling a first sensor to a superabrasive cutter;

communicably coupling a second sensor to a rock;
rotating the superabrasive cutter that is attached to a spinning wheel, the spinning wheel comprising an axis of rotation about which the superabrasive cutter is rotated and a diameter of cutter rotation through which the superabrasive cutter is rotated;
moving the rock having a surface that is positioned normal to the axis of rotation of the spinning wheel and is milled by the superabrasive cutter, wherein the rock is brought into contact with the superabrasive cutter and is fed in a direction normal to the axis of rotation of the spinning wheel, wherein the rock comprises a height evaluated in a plane of the diameter of cutter rotation, wherein the height of the rock is less than the diameter of cutter rotation, such that the superabrasive cutter is brought into and out of contact with the rock along the milled surface; and
monitoring a wear condition of the superabrasive cutter using the first sensor and the second sensor.

11. The method of claim 10, wherein the second sensor is a vibration sensor.

12. The system of claim 11, wherein the vibration of the rock increases with increasing wear scar size.

13. The method of claim 10, wherein the first sensor is a temperature sensor.

14. The system of claim 13, wherein the temperature of the superabrasive cutter increase with increasing wear scar size.

15. The method of claim 10, wherein the superabrasive cutter has a superabrasive volume.

16. The method of claim 15, wherein the superabrasive volume has superabrasive particles.

17. The method of claim 15, wherein the superabrasive cutter has a metal carbide attached to the superabrasive volume via an interface between the superabrasive volume and the metal carbide.

18. The method of claim 17, wherein the metal carbide is cemented tungsten carbide.

19. The method of claim 18, further comprising continuing wearing the rock by the superabrasive cutter until the cutter wears to at least about 4 mm of the tungsten carbide.

* * * * *